United States Patent [19]

Lebugle et al.

[11] Patent Number: 5,709,875
[45] Date of Patent: Jan. 20, 1998

[54] IMPLANTABLE BIODEGRADABLE MATERIAL AND PROCESS FOR ITS PRODUCTION

[75] Inventors: Albert Lebugle, Saint Orens; Anne Julia, Montastruc la Conseillère; Fernand Rodriguez, Castanet; Paul Bonnevialle, Toulouse, all of France

[73] Assignee: Centre National de la Recherche Scientifique (C.N.R.S), Paris, France

[21] Appl. No.: 316,062

[22] Filed: Sep. 30, 1994

Related U.S. Application Data

[63] Continuation of Ser. No. 877,171, Jun. 26, 1992, abandoned.

[30] Foreign Application Priority Data

Oct. 26, 1990 [FR] France ................... 90 13424

[51] Int. Cl.$^6$ ............... A61K 9/10; A61K 47/36
[52] U.S. Cl. ............. 424/426; 424/488; 424/602
[58] Field of Search ................. 424/426, 409, 424/484, 488, 464, 602; 514/777, 778; 523/109, 115; 623/16–23; 106/217.01

[56] References Cited

U.S. PATENT DOCUMENTS

| | | | |
|---|---|---|---|
| 4,497,075 | 2/1985 | Niwa et al. | 623/16 |
| 4,772,468 | 9/1988 | Pfirrmann | 424/602 |
| 4,861,733 | 8/1989 | White | 623/16 |
| 4,863,472 | 9/1989 | Tormala et al. | 623/16 |
| 4,917,702 | 4/1990 | Scheicher et al. | 623/16 |
| 4,988,358 | 1/1991 | Eppley et al. | 623/16 |
| 5,034,059 | 7/1991 | Constantz | 424/423 |
| 5,073,373 | 12/1991 | O'Leary et al. | 424/422 |

FOREIGN PATENT DOCUMENTS

| | | |
|---|---|---|
| 24025 | of 1984 | Australia . |
| 102165 | of 1990 | Japan . |
| 23967 | of 1990 | Japan . |

OTHER PUBLICATIONS

A French–English Dictionary For Chemists, A.M. Patterson, John Wiley & Sons, NY, 2nd Ed. 1963, p. 99.

*Primary Examiner*—Edward J. Webman
*Attorney, Agent, or Firm*—Harold H. Dutton, Jr.

[57] ABSTRACT

The invention relates to a material which can be implanted in living tissue, in particular bony tissue, and having a rate of biodegradation adapted to the rate at which the tissue is regenerated; this material may comprise an active substance in order to achieve a therapeutic effect of prolonged duration. This material comprises (a) a calcium phosphate with apatitic or triclinic structure comprising $HPO_4$ and $PO_4$ groups, (b) a biodegradable oside or polyoside, in particular dextran, (c) if required, an active substance comprising amine groups such as netilmicin and/or gentamicin in sulphate form. The implantable material according to the invention may be produced without heat by compacting its various constituents in the powdery state.

13 Claims, No Drawings

IMPLANTABLE BIODEGRADABLE MATERIAL AND PROCESS FOR ITS PRODUCTION

This application is a continuation of Ser. No. 07/877171, filed Jun. 26, 1992 now abandoned.

The invention relates to a new material capable of being implanted in a living tissue, in particular bony tissue. It is intended to provide a material having a rate of biodegradation adapted to the regeneration of tissue and capable, if required, of being combined with an active substance in order to produce a prolonged therapeutic effect.

BACKGROUND AND OBJECTS OF THE INVENTION

Materials or matrices for implantation in living tissues, especially bony tissues, are known, such as enable making good a tissue "defect" and, if required, the release of an active substance. Said implantation matrices can currently be classified in four categories.

In the first place, there exist non-biodegradable matrices such as certain polymers (for example polymethyl methacrylate PMMA) which are used for local release of active substances, thus avoiding their administration in a systemic way. These matrices have the disadvantage of necessitating a further surgical intervention in order to extract them after release of the active substance (patent FR 74.13342). Furthermore, a very low fraction of the initial active substance is released (about 6%).

Other older matrices such as matrices based on calcium sulphate are biodegradable but their rate of degradation is fixed and cannot be adapted to the rate of regeneration of the tissue in question; their degradation being generally too rapid for the bony tissues, they frequently entail the occurrence of "defects" in said tissues. They also have the disadvantage of not promoting regeneration of the tissue.

Implantation matrices of another type are the polylactic-glycolic matrices PLGA, which have the advantage of enabling, by relative dosage of the two components, some modulation of their rate of degradation in order to adapt the latter to the rate at which the tissue in question is regenerated. However, these matrices do not promote the regeneration of the tissues in any way and, which is worse, they lead to inflammatory reactions, owing to depolymerisation in the course of degradation (formation of acids).

The last category of implantation matrices is constituted by matrices based on tricalcium or apatitic phosphate, the cohesion of which is ensured either by calcination (porous ceramic such as proposed in patent DE 2.807.132) or by a binder such as collagen or elastin (patent DE 3.206.726). These matrices promote bony regeneration but their biodegradability is very slow and cannot be modulated. This being the case, they impede normal reconstitution of the tissues in spite of their positive effect on osteogenesis. Moreover, when combined with an active substance of soluble type, for example gentamicin sulphate, they lead to excessively rapid release of the substance, which is a major disadvantage with substances of high toxicity and/or in case of a treatment necessitating prolonged application. In order to counteract these disadvantages, the active substance has occasionally been converted into a salt of low solubility (for example hesperidin phosphate as mentioned in patent DE 3.206.706): since a certain hydrophobic character is conferred to the product, one thus delays its release at the site but at the start of implantation this release is very low and becomes efficacious only after a considerable lapse of time, which is a severe disadvantage when treating an ailment.

Moreover, patent EP 0.147.021 describes a liquid medical compound (aqueous suspension) which can be introduced into the cavity of a bone by means of a drain tube in order to treat an ailment (osteomyelitis) locally by release of the active substance. However, this is not a material for implantation capable of temporarily replacing the tissue but a simple solution without any mechanical characteristic, the sole purpose of which is to release the active substance locally and then to drain away. Furthermore, said active substance is released immediately and does not have any prolonged effect over a period of time.

The present invention is intended to provide a new implantable material of the type based on calcium phosphate, said material being perfectly biocompatible and capable of promoting osteogenesis without any disadvantageous reaction such as an inflammatory reaction; the essential object of the invention is to provide an implantable material offering mechanical characteristics wherein it can be substituted for defective tissue temporarily, while benefiting from a rate of biodegradation adjusted to the rate at which said tissue is regenerated.

Another object of the invention is to combine the above material with an active substance endowed with groups appropriate to ensure progressive release of said substance, with a prolonged therapeutic effect over a period of time.

Another object is to provide a material for implantation which can be easily manufactured without heat by compaction of these various constituents.

DESCRIPTION OF THE INVENTION

To this end, the process intended by the invention for producing the above implantable material consists in mixing a calcium phosphate with a biodegradable ose or polyoside, said process being characterised in that:

- use is made of a calcium phosphate with apatitic or triclinic structure comprising both $HPO_4$ groups and $PO_4$ groups,
- a proportion of oside or polyoside is mixed, which increases with the rate at which degradation of the material is required.

The calcium phosphate used may comprise different cationic calcium substituents (magnesium, sodium) or anionic substituents of phosphate ions (carbonates) or hydroxyl ion substituents (chlorine); it may also be non-substituted and have the formula

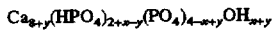

$$Ca_{8+y}(HPO_4)_{2+x-y}(PO_4)_{4-x+y}OH_{x+y}$$

where y is larger than or equal to 0 and smaller than or equal to 2 and x is larger than or equal to 0 and smaller than 1.

The calcium phosphate of the above type and the oside or polyoside are preferably mixed in powder form, whereupon they are compacted in order to impart to them a predetermined shape. The implants thus produced may either be located in the tissue, in particular bony tissue, after preparing a seat suitable for the location of the "defect", or they may be immobilised within an existing cavity of the tissue by means of a biodegradable binding agent such as calcium sulphate or a binding agent based on phosphate.

The tests have shown that the degradation of the implantable material according to the invention varies in duration between several days (3–4 days) and a much longer time amounting to several months (10–12 months) depending on the proportion of ose or polyoside mixed with the phosphate. Different oses or polyosides may be used, and the degradation times increase with the molecular mass of this compound; one can for instance modulate the rate of biodegradation by the choice of ose or polyoside and by adjustment of its proportion in relation to the phosphate. In particular, dextran may be used by way of polyoside, the proportion of the latter being modulated between 1% and 30%, depending on the required rate of degradation; the latter increases with the proportion of dextran, and hence the larger the amounts of dextran mixed with the phosphate, the shorter will be the degradation times.

Moreover, the implantable material according to the invention may be combined with an active substance capable of producing a required therapeutic effect. According to one characteristic of the invention, use is made of an active substance comprising amine groups, which enable it to be fixed on the calcium phosphate provided with $HPO_4$ and $PO_4$ groups.

Hence the three constituents of the material according to the invention co-operate to bring about progressive release of the active substance. It has been possible to show that the fixation of the active substance on the phosphate is associated with the presence of both $HPO_4$ and $PO_4$ groups, probably as a result of adsorption brought about by the amine groups of said substance, said fixation being such as to lead subsequently to progressive release of said substance at the site of implantation. Surprisingly, the tests have made it possible to show that the presence of osides or polyosides such as dextran had the characteristic of regularising said release, making it possible to achieve immediately efficacious rates and to prolong said release over a period of several weeks, at a substantially constant rate. (The opposite effect might have been expected, since the osides or polyosides are highly soluble compounds).

Incidentally, it must be stressed that the osides or polyosides act as plasticisers during compaction of the material, improving its cohesion considerably; this seems to be due to the fact that the presence of this compound leads to a considerable increase in the size of the phosphate grains, a phenomenon intensifying the cohesion; said phenomenon of an increase in the size of the grains makes it possible to explain, at least partly, the reduction and regularisation of the rate at which the active substance is released; this substance, which is fixed owing to the $HPO_4$ and $PO_4$ groups of the phosphate, is released with greater difficulty inside large grains; moreover, the reduction of the specific surface of the grains, as their size increases, is a factor reducing the dissolution kinetics where the grains join.

Summarizing, in the invention the retarding effect and its characteristics (substantially constant release rate and prolonged effect over a period of time) are achieved by fixing the active substance on the matrix; this substance, which is used preferably in soluble form, is released by rupture of said bonds or interactions, with the oside or polyoside exerting a positive influence on the strength of the latter. (By contrast, the matrix specified in the above-mentioned patent DE 3.206.726 is inert in relation to the active substance and the retarding effect of the medicament is due to the insoluble form given to the active substance).

The calcium phosphate, the active substance and the oside or polyoside are preferably mixed in powder form and compacted; this easy-to-apply compacting process confers to the material good cohesion at conventional compacting pressures: the material can therefore be produced without heat, without altering the active substance (which is generally sensitive to heat).

With a preferred form of the material, one chooses by way of phosphate an apatitic octacalcium phosphate with the formula: $Ca_8(HPO_4)_{2+x}(PO_4)_{4-x}(OH)_x$, where x is larger than zero and smaller than 1. That is a phosphate which had the largest number of $HPO_4$ groups per formulary unit; within the scope of the invention it offers the best performances (better fixation of the active substance per unit of material mass, improved galenical characteristics). Good results are achieved by choosing a value of about 0.5 (within ±20%) for the parameter x in which case the formula of the material used is roughly as follows:

$$Ca_8(HPO_4)_{2.5}(PO_4)_{3.5}(OH)_{0.5}$$

It is as such known how to produce such phosphates; examples are provided below together with references to publications describing methods of production.

The mixed active substance advantageously has the form of a soluble salt, in particular in the case of netilmicin and/or gentamicin in sulphate form (which is the most soluble form thereof); these substances are used very frequently for the treatment of bone ailments owing to their large spectrum of efficaciousness.

By way of non-restrictive example, the material according to the invention may comprise in a mixture of apatitic octacalcium phosphate with the above formula (parameter x close to 0.5), dextran and netilmicin and/or gentamicin in sulphate form, the proportions being as follows:

the proportion by weight of dextran amounts to between 1% and 30% of the mixture (depending on the rate of biodegradation required), the proportion by weight of active substance amounts to between 0.1% and 30% of the mixture (depending on the activity of the substance and the required effects).

DETAILED DESCRIPTION OF THE PREFERRED EMBODIMENTS

The following description presents examples of implantation materials according to the invention and illustrates their galenical, pharmacokinetic and physiological characteristics as well as the evolution of the latter in accordance with their composition.

EXAMPLE 1

Preparation of phosphate OCPa 100 g octacalcium phosphate with an apatitic structure (OCPa) according to formula $Ca_8(HPO_4)_{2.5}(PO_4)_{3.5}(OH)_{0.5}$ are prepared by precipitation in a medium obtained by adding the same volumes of ethanol and aqueous solution on the basis of a solution (A) of calcium salt and an ammoniacal solution (B) containing orthophosphate ions. The number of calcium ions contained in solution (A) is equal to the number of phosphate ions in solution (B). Solution (A) is poured rapidly, while stirring, at 37° C. into solution (B). After formation the precipitate is filtered by means of a Büchner funnel, washed with a basic solution and kiln-dried at 80° C.. A powder is obtained, which has a quasi-homogeneous granular matrix distribution between 0.5 and 0.08 mm and a flow time (rheological analysis) of 4 sec (AFNOR standards). The study of the compression of this powder carried out with the aid of an alternative "Korsch-type EKO" compressing machine equipped with strain gauges making it possible to measure the compression parameters has shown 50% aggregation work and 84% transmission.

Production of a material without therapeutic effect

Dextran (supplier "SIGMA", quality "clinical grade") was added in variable proportion to octacalcium phosphate prepared as above; the proportion of dextran in the mixture was caused to vary between 1% and 30% (a comparative test being carried out in the absence of dextran). The two compounds are mixed thoroughly and compressed at a pressure of about 2000 DaN/cm², at normal temperature. The compressed tablets obtained, with a diameter of 6 mm and a thickness of 2 mm, have in the presence of dextran a Stockes hardness 15 and zero friability whereas in the absence of dextran (pure OCPa) the hardness amounts only to 10 and the friability to 1%.

EXAMPLE 2

80 g octacalcium phosphate prepared as in example 1 are mixed thoroughly with 20 g glucose and compressed under the preceding conditions. The Stockes hardness of the compressed tablets obtained amounts to 14 and the friability to zero.

EXAMPLE 3

Production of a material with therapeutic effect 90 g octacalcium phosphate prepared as in example 1, 5 g netilmicin sulphate and 5 g dextran are mixed thoroughly and compressed at a pressure of 2000 DaN/cm² at normal temperature. The compressed tablets obtained, with a diameter of 6 mm and a thickness of 2 mm have a Stockes hardness 15 and zero friability.

EXAMPLE 4

85 g octacalcium phosphate prepared as in example 1, 5 g netilmicin sulphate and 10 g dextran are mixed thoroughly and compressed at a pressure of 2000 DaN/cm² at normal temperature to the shape of tablets with 6 mm diameter and 2 mm thickness. The measured Stockes hardness amounts to 18 and the friability to zero.

EXAMPLE 5

80 g octacalcium phosphate prepared as in example 1, 5 g netilmicin sulphate and 15 g dextran are mixed thoroughly and compressed at a pressure of 2000 DaN/cm² at normal temperature to the shape of tablets with 6 mm diameter and 2 mm thickness. The measured Stockes hardness amounts to 18 and the friability to zero.

EXAMPLE 6

75 g octacalcium phosphate prepared as in example 1, 5 g netilmicin sulphate and 20 g dextran are mixed thoroughly and compressed at a pressure of 2000 DaN/cm² at normal temperature to the shape of tablets with 6 mm diameter and 2 mm thickness. The measured Stockes hardness amounts to 17 and the friability to zero.

EXAMPLE 7

In this example both the proportion of netilmicin and the proportion of phosphate were caused to vary in such a way that the sum of the two remained constant and equal to 95%, the proportion of dextran being constant and equal to 5%.

The octacalcium phosphate was produced in the same way as in example 1. Four medicaments were obtained in succession, with the following proportions:

85% octacalcium phosphate, 10% netilmicin sulphate and 5% dextran,
80%, 15% and 5%, respectively
75%, 20% and 5%, respectively
70%, 25% and 5%, respectively.

The compaction was similar to that in the preceding examples and resulted in a Stockes hardness substantially identical and equal to 17 and in zero friability.

EXAMPLE 8

90 g tricalcium phosphate with apatitic structure and the formula $Ca_9(HPO_4)(PO_4)_5OH$ were prepared according to a method analogous with that in example 1, the difference being that the ratio between the number of calcium ions in solution (A) and the number of phosphorus ions in solution (B) no longer amounts to 1 but to 1.6; 5 g netilmicin sulphate and 5 g dextran were mixed thoroughly with said 85 g tricalcium phosphate and compressed at a pressure of 2000 DaN/cm² and at standard temperature. The measured Stockes hardness amounts to 13 and the friability to 0.5% by weight.

EXAMPLE 9

Octacalcium phosphate with a triclinic structure and the formula $Ca_8(HPO_4)_2(PO_4)_4$ was prepared according to BROWN's method, which consists in slow hydrolysis of brushite $Ca(HPO_4)2H_2O$ in a solution of 0.5M sodium acetate at 40° C. (W. BROWN et al., J. Am. Chem. Soc. 79—p. 5318–9, 1957), 85 g of said phosphate, 5 g netilmicin sulphate and 10 g dextran were mixed thoroughly and compressed under the preceding conditions. The hardness of the compressed tablets amounts to 15 and the friability to zero.

EXAMPLE 10

90 g octacalcium phosphate prepared as in example 1, 5 g gentamicin sulphate and 5 g dextran were mixed thoroughly and compressed as above. The hardness of the compressed tablets amounts to 15 and their friability to zero.

EXAMPLE 11

85 g octacalcium phosphate with apatitic structure prepared as in example 1, 5 g netilmicin sulphate and 10 g glucose were mixed thoroughly and compressed. The hardness of the compressed tablets amounts to 16 and their friability to 0.5%.

EXAMPLE 12

The influence of the proportion of dextran on the degradation of the material produced in example 1 was studied by implantation in the proximal metaphyseal region of a dog's ulna, in which a cavity had been drilled, as well as in the distal metaphyseal zone of the radius. It has been found, by radiography and anatomopathological study, that after two months the implanted materials have degraded only at the periphery if the proportion of dextran is zero (test), whereas the degradation increases with said proportion. When the latter amounts to between 20 and 30%, the implant has disappeared and has been replaced by spongy bone. The control radiographs did not, at any time during a period of two months, show a "defect" between the implant and the bone.

EXAMPLE 13

The influence of the characteristics of the oside or polyoside on the degradation of the materials produced in examples 1 and 2 was studied as in example 12, by implantation in dogs. It was found that with 20% glucose the implant was totally degraded after two months and that a bony "defect" remains, whereas with dextran the implant is degraded but has been replaced by bone. At the proportion studied (20%), the materials produced with glucose are degraded too quickly for the bony tissues in question (ulna and radius) and do not enable any bony regrowth, whereas with dextran, where the rate of degradation is adapted to that of bone regeneration, such regrowth does take place.

EXAMPLE 14

The influence of the proportion of dextran on the kinetics of netilmicin release was studied in vitro with the aid of a dissolution apparatus. The study was carried out using compressed tablets prepared in examples 3 to 6. The method of release was as follows: with each medicament two compressed 100 mg tablets were caused to dissolve in the tank of the apparatus, which contained 500 ml distilled water and was thermostatically controlled at 37° C. subject to continuous stirring (60 rev/min). Samples were taken periodically. The netilmicin was dosed by immuno-enzymology.

It has been found that paradoxically the amount of antibiotic released after 50 h dissolution at 37° C. diminishes as the proportion of dextran increases, although the latter is hydrophilic. However, this hydrophilic character exerts an influence at the start of the kinetic process, when it promotes advantageously the release of netilmicin making it possible to reach high concentrations, above the minimum inhibiting concentration, very quickly.

EXAMPLE 15

The influence of the characteristics of the antibiotic on the kinetics of release was studied in vitro with the aid of a dissolution apparatus using compressed tablets produced in example 3 and, by way of comparison, using compressed tablets produced under the same conditions but substituting for the netilmicin an active substance devoid of amine groups, i.e. oxacillin. This study reveals that with oxacillin total and very rapid release (1 h) takes place, whereas under the same experimental conditions only 30% netilmicin are released after 50 h. The presence of amine groups in the aminosides exerts a decisive influence on the mechanisms governing the release of active substance.

EXAMPLE 16

The influence of the chemical composition of the phosphate on the kinetics of aminoside release was studied invitro with the aid of a dissolution apparatus using compressed tablets produced in examples 3 and 8 and, by way of comparison, using compressed tablets produced under the same conditions but substituting for the octacalcium or tricalcium phosphate with apatitic structure hydroxyapatite devoid of the $HPO_4$ group (formula $Ca_{10}(PO_4)_6(OH)_2$). The latter compound was prepared according to TROMBE's method, which consists in pouring slowly a solution of diammonium phosphate into a solution of calcium acetate, the ratio between the number of calcium ions and the number of phosphorus ions in these solutions being equal to 1.66 (J. C. TROMBE, Ann. Chim. 8, 251, 1973). This study proves that the kinetics of release are directly associated with the proportion of hydrogen phosphate ions, $HPO_4$, in the phosphates studied. Hence, with hydroxyapatite (proportion of $HPO_4$ zero) the aminoside is released virtually immediately, whereas with tricalcium phosphate (proportion of $HPO_4$ equal to 1) it is delayed, the proportion released after 50 h amounting to 60%, and with octacalcium phosphate with apatitic structure extremely delayed, the amount released after 50 h being 30% (proportion of $HPO_4$ close to 2.5).

EXAMPLE 17

The influence of the characteristics of the oside used on the kinetics of release of the active substance was studied in vitro under the same conditions as those in example 15 using compressed tablets produced in examples 4 and 11. This comparative study has shown that the osides used exert a substantially comparable effect on the kinetics of release, the preferred substance however being dextran, which causes a slower release.

EXAMPLE 18

The influence of the formulation of the compressed tablets on their behaviour in vivo was studied by implanting them at a bony site in animals, i.e. rabbits and dogs, and studying their biocompatibility and their rate of degradation. This study was carried out with the aid of compressed tablets produced in examples 3 to 11; moreover, by way of comparison, medicaments were produced under the same conditions with proportions of dextran and netilmicin which were either too low (total proportion less than 1%) or too high (total proportion higher than 35%). When the total proportion of dextran and netilmicin is too low the implant, although perfectly tolerated, is not completely degraded after three months implantation. In this example of implantation at a bony site the implant was degraded too quickly when the total proportion of dextran and netilmicin was too high, leaving behind a bony "defect". On the other hand, when the global proportion of dextran and netilmicin amounted to between 4% and 35% the perfectly biocompatible implant was largely degraded after three months and replaced by spongy bone; the best results were achieved with the medicaments produced in examples 3 to 6. Hence the formulation of the compressed tablets makes it possible to adjust the rate of degradation to the required object.

We claim:

1. A process for producing a powdered composition for implantation in human or animal tissue comprising providing about 1% to about 30% of a powdered biodegradable ose or polyoside and powdered calcium phosphate having an apatitic or triclinic structure and containing both $HPO_4$ and $PO_4$ groups to form a mixture, adding to said mixture an active substance having amine groups for fixing the active substance on the $HPO_4$ and $PO_4$ groups of the calcium phosphate and mixing the substances together.

2. A process as in claim 1 and wherein said calcium phosphate is selected from the group consisting of compounds having the formula

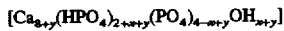

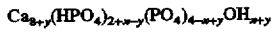

wherein $0 \leq y \leq 2$ and wherein $0 \leq x \leq 1$, provided that x IJ 0 if y=2 and y IJ 2 if x=0.

3. A process as in claim 1 and wherein the ose or polyoside is initially in powder form, and after the mixing step, compacting the mixture.

4. A process as in claim 2 and wherein the ose or polyoside is initially in powder form, and after the mixing step, compacting the mixture.

5. A compatible powder composition implantable in living tissue and having a prolonged therapeutic effect comprising a mixture of a first compound selected from the group consisting of calcium phosphates having an apatitic or triclinic structure and containing both $HPO_4$ and $PO_4$ groups, and a second compound selected from the group consisting of about 1% to about 30% of a biodegradable ose or polyoside, and at least one active substance having amine groups and for producing the therapeutic effect.

6. A composition as in claim 5 and wherein the calcium phosphate is a phosphate of the formula $$Ca_{8+y}(HPO_4)_{2+x-y}(PO_4)_{4-x+y}OH_{x+y}$$

wherein $0 \leq y \leq 2$ and wherein $0 \leq x \leq 1$, provided that $x \neq 0$ if $y=2$ and $y \neq 2$ if $x=0$.

7. An implantable composition as in claim 5 and wherein said calcium phosphate consists of an apatitic octacalcium phosphate having the formula $$Ca_8(HPO_4)_{2+x}(PO_4)_{4-x}(OH)_x$$

where x is greater than zero and less than 1.

8. An implantable composition as in claim 7 in which the calcium phosphate is apatitic octacalcium phosphate in which x is about 0.5 and has the formula $$Ca_8(HPO_4)_{2.5}(PO_4)_{3.5}(OH)_{0.5}.$$

9. An implantable composition as in claim 5 and wherein the active substance is a water soluble salt.

10. An implantable composition as in claim 5 and wherein the active substance is a soluble salt of netilmicin or gentamicin.

11. An implantable composition as in claim 5 comprising between 1% and 30% of dextran by weight of the mixture and between 0.1% and 30% by weight of the mixture of said active substance.

12. A process for producing a powdered composition for implantation in human or animal tissue comprising providing a quantity of a powdered biodegradable ose or polyoside and powdered calcium phosphate having an apatitic or triclinic structure and containing both $HPO_4$ and $PO_4$ groups to form a mixture, adding to said mixture an active substance having amine groups for fixing the active substance on the $HPO_4$ and $PO_4$ groups of the calcium phosphate and mixing the substances together.

13. An implantable composition as in claim 2 and wherein the proportion by weight of dextran is between 1% and 30% of the mixture.

* * * * *